(12) United States Patent
Santi et al.

(10) Patent No.: US 11,730,836 B2
(45) Date of Patent: Aug. 22, 2023

(54) SYNERGISTIC CANCER TREATMENT

(71) Applicant: ProLynx LLC, San Francisco, CA (US)

(72) Inventors: Daniel V. Santi, San Francisco, CA (US); Shaun Fontaine, Concord, CA (US)

(73) Assignee: ProLynx LLC, San Francisco, CA (US)

( * ) Notice: Subject to any disclaimer, the term of this patent is extended or adjusted under 35 U.S.C. 154(b) by 124 days.

(21) Appl. No.: 16/961,640

(22) PCT Filed: Jan. 11, 2019

(86) PCT No.: PCT/US2019/013314
§ 371 (c)(1),
(2) Date: Jul. 10, 2020

(87) PCT Pub. No.: WO2019/140271
PCT Pub. Date: Jul. 18, 2019

(65) Prior Publication Data
US 2020/0397778 A1 Dec. 24, 2020

Related U.S. Application Data

(60) Provisional application No. 62/716,796, filed on Aug. 9, 2018, provisional application No. 62/716,788, filed on Aug. 9, 2018, provisional application No. 62/711,423, filed on Jul. 27, 2018, provisional application No. 62/711,421, filed on Jul. 27, 2018, provisional application No. 62/700,147, filed on Jul. 18, 2018, provisional application No. 62/674,483, filed on May 21, 2018, provisional application No. 62/617,095, filed on Jan. 12, 2018.

(51) Int. Cl.
| | |
|---|---|
| *A61K 51/06* | (2006.01) |
| *A61K 47/60* | (2017.01) |
| *A61K 9/51* | (2006.01) |
| *A61P 35/00* | (2006.01) |
| *A61K 31/4745* | (2006.01) |
| *A61K 45/06* | (2006.01) |
| *B82Y 5/00* | (2011.01) |

(52) U.S. Cl.
CPC ............ *A61K 51/065* (2013.01); *A61K 9/51* (2013.01); *A61K 31/4745* (2013.01); *A61K 47/60* (2017.08); *A61P 35/00* (2018.01); *A61K 45/06* (2013.01); *B82Y 5/00* (2013.01)

(58) Field of Classification Search
None
See application file for complete search history.

(56) References Cited

U.S. PATENT DOCUMENTS

| | | |
|---|---|---|
| 7,850,990 B2 | 12/2010 | Tardi et al. |
| 8,299,089 B2 | 10/2012 | Zhao et al. |
| 8,680,315 B2 | 3/2014 | Santi et al. |
| 8,703,907 B2 | 4/2014 | Ashley et al. |
| 8,754,190 B2 | 6/2014 | Ashley et al. |
| 8,946,405 B2 | 2/2015 | Ashley et al. |
| 9,271,931 B2 | 3/2016 | Tardi et al. |
| 9,387,254 B2 | 7/2016 | Santi et al. |
| 10,016,411 B2 | 7/2018 | Ashley et al. |
| 2004/0176270 A1 | 9/2004 | Chen et al. |
| 2005/0112088 A1 | 5/2005 | Zhao et al. |
| 2006/0067910 A1 | 3/2006 | Kitagawa et al. |
| 2010/0126866 A1 | 5/2010 | Kemptner et al. |
| 2010/0305149 A1 | 12/2010 | Yurkovetskiy et al. |
| 2013/0116407 A1 | 5/2013 | Ashley et al. |
| 2013/0310448 A1 | 11/2013 | Wang et al. |
| 2014/0357659 A1 | 12/2014 | Ute et al. |
| 2016/0063508 A1 | 3/2016 | Fukushima et al. |
| 2016/0185805 A1 | 6/2016 | Shuhendler et al. |
| 2016/0375142 A1 | 12/2016 | Chimmanamada et al. |
| 2017/0049767 A1 | 2/2017 | Blanchette et al. |
| 2017/0313781 A1 | 11/2017 | Serengulum et al. |
| 2018/0280551 A1 | 10/2018 | Rashidian et al. |

FOREIGN PATENT DOCUMENTS

| | | |
|---|---|---|
| AU | 2016239270 B2 | 11/2022 |
| CN | 106084005 | 11/2016 |
| CN | 107050471 | 8/2017 |
| EP | 2319855 A1 | 5/2011 |
| JP | 2013542997 A | 11/2013 |
| JP | 2016531895 A | 10/2016 |
| WO | WO 2004039869 A1 | 5/2004 |
| WO | WO 2005/007136 | 1/2005 |
| WO | WO 2005/028539 | 3/2005 |

(Continued)

OTHER PUBLICATIONS

Santi et al., Journal of Medicinal Chemistry (2014), 57, pp. 2303-2314.*
Zander et al., PLoS ONE (2012), 7(9), e45248 (11 pages).*
Boerner et al., PLoS ONE (2015), 10(3), e0119614 (9 pages).*
Aris et al., Cancer Research (2012), 72(4), pp. 979-989.*
Abal et al. "Enhanced sensitivity to irinotecan by Cdk1 inhibition in the p53-deficient HT29 human colon cancer cell line." *Oncogene* (2004) 23.9: 1737-1744.
Beckford Vera et al. "PET Imaging of the EPR Effect in Tumor Xenografts Using Small 15 nm Diameter Polyethylene Glycols Labeled with Zirconium-89Imaging of the EPR Effect in Tumors Using 89Zr-Labeled PEG." *Molecular Cancer Therapeutics* (2020) 19.2: 673-679.
Brandsma et al. "Directing the use of DDR kinase inhibitors in cancer treatment." *Expert opinion on investigational drugs* (2017) 26.12: 1341-1355.

(Continued)

*Primary Examiner* — Brian J Davis
(74) *Attorney, Agent, or Firm* — Morrison and Foerster LLP

(57) ABSTRACT

Conjugates of topoisomerase I inhibitors linked to a macromolecule through a linkage that undergo beta elimination in situ in combination with one or more of an assessed defect in DNA damage response (DDR) in a subject bearing cancer, a cell cycle checkpoint inhibitor and/or a DDR inhibitor provides improved outcomes for cancer-bearing subjects.

10 Claims, 4 Drawing Sheets

(56) References Cited

FOREIGN PATENT DOCUMENTS

| WO | WO 2008/034124 | 3/2008 |
|---|---|---|
| WO | WO 2010/048018 | 4/2010 |
| WO | WO 2011/063158 | 5/2011 |
| WO | WO 2011/140376 | 11/2011 |
| WO | WO 2011/140393 | 11/2011 |
| WO | WO 2012/029076 | 3/2012 |
| WO | WO 2012/074754 | 6/2012 |
| WO | WO 2012/088282 | 6/2012 |
| WO | WO2013/049719 | 4/2013 |
| WO | WO 2013/132485 | 9/2013 |
| WO | WO 2015/051307 | 4/2015 |
| WO | WO 2015/118338 | 8/2015 |
| WO | WO 2015/183876 | 12/2015 |
| WO | WO 2016/028636 | 2/2016 |
| WO | WO 2016/164578 | 10/2016 |
| WO | WO 2016/176462 | 11/2016 |
| WO | WO 2017/031445 | 2/2017 |
| WO | WO 2017/059397 | 4/2017 |
| WO | WO 2017105565 A2 | 6/2017 |
| WO | WO 2017/151554 | 9/2017 |
| WO | WO 2017172678 A1 | 10/2017 |
| WO | WO 2017/189961 | 11/2017 |

OTHER PUBLICATIONS

Chen et al. "A Phase I study of olaparib and irinotecan in patients with colorectal cancer: Canadian Cancer Trials Group IND 187." *Investigational new drugs* (2016) 34.4: 450 absuact.

"Enzon Announces Discontinuation of PEG-SN38 Program in Metastatic Colorectal Carcinoma in Light of Evolving Standards of C," *Fierce Pharma* (2022) 1-8.

Futami et al. "Increased chemotherapeutic activity of camptothecin in cancer ceiis by siRNA-induced silencing of WRN helicase," *Biological and Pharmaceutical Bulletin* (2007) 30.10: 1958-1961.

Gray et al. "Combination of HDAC and topoisomerase inhibitors in small cell lung cancer." *Cancer biology & therapy* (2012) 13.8: 614-622.

Grohar et al. "Dual Targeting of EWS-FLI1 Activity and the Associated DNA Damage Response with Trabectedin and SN38 Synergistically Inhibits Ewing Sarcoma Cell GrowthTrabectedin and SN38 Are Synergistic in Ewing Sarcoma Cells." *Clinical Cancer Research* (2014) 20.5: 1190-1203.

Josse et al. "ATR inhibitors VE-821 and VX-970 sensitize cancer cells to topoisomerase I inhibitors by disabling DNA replication initiation and fork elongation responses." *Cancer research* (2014) 74.23: 6968-6979.

Knijnenburg et al. "Genomic and molecular landscape of DNA damage repair deficiency across The Cancer Genome Atlas." *Cell reports* (2018) 23.1: 239-254.

Koizumi et al. "Novel SN-38—incorporating polymeric micelles, NK012, eradicate vascular endothelial growth factor-secreting bulky tumors." *Cancer research* (2006) 66.20: 10048-10056.

Li et al. "A generic 89Zr labeling method to quantify the in vivo pharmacokinetics of liposomal nanoparticles with positron emission tomography." *International Journal of Nanomedicine* (2017)12: 3281.

Ma et al. "A phase II study of UCN-01 in combination with irinotecan in patients with metastatic triple negative breast cancer." *Breast cancer research and treatment* 137.2 (2013): 483-492.

Morton et al. "Establishment of human tumor xenografts in immunodeficient mice." *Nature protocols* (2007) 2.2: 247-250.

Ovejera et al. "Chemotherapy of human tumor xenografts in genetically athymic mice." *Annals of Clinical & Laboratory Science* (1978) 8.1: 50-56.

Patnaik et al. "Phase I dose-escalation study of EZN-2208 (PEG-SN38), a novel conjugate of poly (ethylene) glycol and SN38, administered weekly in patients with advanced cancer." *Cancer chemotherapy and pharmacology* (2013) 71.6: 1499-1506.

Ramogida et al. "Tumour targeting with radiometais for diagnosis and therapy." *Chemical Communications* (2013)49.42: 4720-4739.

Samol et al. "Safety and tolerability of the poly (ADP-ribose) polymerase (PARP) Inhibitor, olaparib (AZD2281) in combination with topotecan for the treatment of patients with advanced solid tumors: a phase I Study." *Investigational new drugs* (2012) 30.4: 1493 abstract.

Sapra et al. "Novel delivery of SN38 markedly inhibits tumor growth in xenografts, including a camptothecin-11-refractory model." *Clinical Cancer Research*(2008)14.6 : 1888-1896.

Wainberg et al. "A multi-arm phase i study of the PI3K/mTOR inhibitors PF-04691502 and gedatolisib (PF-05212384) plus irinotecan or the MEK inhibitor PD-0325901 in advanced cancer." *Targeted oncology* (2017) 12.6: 775-785.

Wilks et al. "Imaging PEG-iike narsoprobes in tumor, transient ischemia, and inflammatory disease models." *Bioconjugate chemistry* (2015)26.6 : 1061-1069.

Verschraegen et al. "A phase I study of the combination of temsirolimus with irinotecan for metastatic sarcoma." *Cancers* (2013) 5.2: 418-429.

Visconnti et al. "Cell cycle checkpoint in cancer: a therapeutically targetable double-edged sword." *Journal of Experimental & Clinical Cancer Research* (2016) 35.1: 1-8.

Zhao et al. "Novel prodrugs of SN38 using multiarm poly (ethylene glycol) linkers." *Bioconjugate chemistry* (2008) 19.4: 849-859.

Bailly et al., "Possible roles of Beta-elimination and Delta-elimination reactions in the repair of DNA containing AP (apurinic/apyrimidinic) sites in mammalian cells," Biochem J. 1988, vol. 253(2), p. 553-9.

Feng et al., "Abstract C54: Combination of PARP inhibitor talazoparib with etirinotecan pegol exhibits synergistic anti-tumor effect in non-BRCA preclinical cancer models," Molecular Cancer Therapeutics, 2015, vol. 14, issue 12, supp 2, C54, 2 pages.

Joralemon, "PEGylated polymers for medicine: from conjugation to self-assembled systems," Chem. Commun., 2010, 46, 1377-1393.

Luo et al., "Nanomedical Engineering: shaping future nanomedicines," Nanomedicine and Nanobiotechnology, (2015), vol. 7, pp. 169-188, 34 pages.

Patil et al., "Checkpoint kinase 1 in DNA damage response and cell cycle regulation," Cell Mol Life Sci. 2013, vol. 70(21), p. 4009-21, 22 pages.

Prolynx, Executive Summary—PLX038: Prolynx's PEG-SN-38. ProLynx. 2016 [online], [Retrieved on Feb. 20, 2019], Retrieved from the Internet: <URL:http://nebula.wsimg.com/2832dae0a82ac9b9b09eb2883bee2945?AccessKeyId=5C5CA0B60D78D12D136C&disposition=0&alloworigin=1>, 2 pages.

Rimar et al., "The Emerging Rile of Homologous Recombination Repair and PARP Inhibitors in Genitourinary Malignancies," Cancer. 2017, vol. 123(11), p. 1912-1924.

Sezaki et al., "Macromolecule-drug conjugates in targeted cancer chemotherapy," Crit Rev Ther Drug Carrier Syst, 1984, 1(1), p. 1-38. Abstract Only.

Shen et al., "BMN 673, a Novel and Highly Potent PARP1/2 Inhibitor for the Treatment of Human Cancers with DNA Repair Deficiency," Clinical Cancer Research, 2013, vol. 19)18):5003-5015.

Sheng et al., "New strategies in the discovery of novel non-camptothecin topoisomerase I inhibitors," Curr Med Chem., 2011, 18(28), pp. 4389-4409.

Silver et al., "Mechanisms of BRCA1 Tumor Suppression," Cancer Discov. 2012, vol. 2(8), p. 679-84.

Teng et al., "Research progress on design principle and application of polyethylene glycol prodrug," China pharmaceutical, 2014, vol. 23, No. 15, 4 pages. English abstract.

Williams et al., "Treatment with the PARP inhibitor, niraparib, sensitizes colorectal cancer cell lines to irinotecan regardless of MSI/MSS status," Cancer Cell Int. 2015, vol. 15(1):14.

Zhang et al., "WEE1 inhibition by MK1775 as a single-agent therapy inhibits ovarian cancer viability," Oncol Lett. 2017, vol. 14(3), p. 3580-3586.

Allen et al., "Drug delivery systems: entering the mainstream," Science (2004) 303:1818-1822. Abstract Only.

(56) References Cited

OTHER PUBLICATIONS

Chauhan et al., "Fluorescent Nanorods and Nanospheres for Real-Time In Vivo Probing of Nanoparticle Shape-Dependent Tumor Penetration," Angew. Chem. Int. Ed. Engl. (2011) 50:11417-11420, 8 pages.
Chauhan et al., "Normalization of tumour blood vessels improves the delivery of nanomedicines in a size-dependent manner," Nat. Nanotechnol. (2012) 7:383 388, 14 pages.
Chauhan et al., "Strategies for advancing cancer nanomedicine," Nat. Mater. (2013) 12:958-962, 14 pages.
Danhier et al., "To exploit the tumor microenvironment: Passive and active tumor targeting of nanocarriers for anti-cancer drug delivery," J. Control Rel. (2010) 148:135-146.
Deri et al., "Alternative Chelator for 89Zr Radiopharmaceuticals: Radiolabeling and Evaluation of 3,4,3-(LI-1,2-HOPO)," J Med Chem (2014) 57:4849-4860.
Dreher et al., "Tumor vascular permeability, accumulation, and penetration of macromolecular drug carriers," J. Natl. Cancer Inst. (2006) 98:335-344.
Eshun et al., "VEGF blockade decreases the tumor uptake of systemic oncolytic herpes virus but enhances therapeutic efficacy when given after virotherapy," Gene Ther. (2010) 17:922-929, 15 pages.
Fischer et al., "$^{89}$Zr, a Radiometal Nuclide with High Potential for Molecular Imaging with PET: Chemistry, Applications and Remaining Challenges," Molecules (2013) 18:6469-6490.
Harrington et al., "Effective targeting of solid tumors in patients with locally advanced cancers by radiolabeled pegylated liposomes," Clin. Cancer Res. (2001) 7:243-254.
Khalifa et al., "Liposomal distribution in malignant glioma possibilities for therapy," Nucl. Med. Commun. (1997) 18:17-23. Abstract Only.
Ma et al., "Tripodal tris(hydroxypyridinone) ligands for immunoconjugate PET imaging with $^{89}$Zr$4^{30}$: comparison with desferrioxamine-B," Dalton Trans (2015) 44:4884-4900.
Maeda et al., "Mechanism of tumor-targeted delivery of macromolecular drugs, including the EPR effect in solid tumor and clinical overview of the prototype polymeric drug Smancs," J. Controlled Release (2001) 74:47-61. Abstract Only.
Matsumura et al., "A new concept for macromolecular therapeutics in cancer chemotherapy: mechanism of tumoritropic accumulation of proteins and the antitumor agent smancs," Cancer Res. (1986) 46:6387-6392.
Perk et al., "p-Isothiocyanatobenzyl-desferrioxamine: a new bifunctional chelate for facile radiolabeling of monoclonal antibodies with zirconium-89 for immuno-PET imaging," Eur. J. Nucl. Med. Mol. I. (2010) 37:250-259.
Singh et al., "Non-Invasive Detection of Passively Targeted Poly-(ethylene glycol) Nanocarriers in Tumors," Molecular Pharmaceutics (2012) 9:144-155, 25 pages.
van de Watering et al., "Zirconium-89 labeled antibodies: a new tool for molecular imaging in cancer patients," Biomed. Res. Int. (2014) 2014:203601, 13 pages.
Majumdar et al., "N-Alkyl-N-alkyloxycarbonylaminomethyl (NANAOCAM) prodrugs of carboxylic acid containing drugs," Bioorg Med Chem Letts (2007) 17:1447-1450. Abstract Only.
Atsumi, et al., "Pharmacokinetics of SN-38 [(+)-(4S)-4,I I-diethyl-4,9-dihydroxy-1Hpyrano[3',4':6,7]-indolizino[,2-b]quinoline-3,14(4H,12H)-dione], an active metabolite of irinotecan, after a single intravenous dosing of 14C-SN-38 to rats," Biol. Pharm. Bull. (1995) 18:1114-1119. Abstract Only.
Kato et al., "Panipenem Does Not Alter the Pharmacokinetics of the Active Metabolite of Irinotecan SN-38 and Inactive Metabolite SN-38 Glucuronide (SN-38G) in Rats," Anticancer Res. (2011) 31:2915-2922.
Santi et al., "Predictable and Tunable Half-life Extension of Therapeutic Agents by Controlled Chemical Release from Macromolecular Conjugates," Proc. Natl. Acad. Sci. USA (2012) 109:6211-6216.
Caldwell et al., "Allometric scaling of pharmacokinetic parameters in drug discovery: can human CL, Vss and tl/2 be predicted from in-vivo rat data?," Eur J Drug Metab Pharmacokinet. (2004) 29:133-143. Abstract Only.
Eldon et al., "Population Pharmacokinetics of NKTR-102, a Topoisomerase Inhibitor-Polymer Conjugate in Patients With Advanced Solid Tumors," American Society of Clinical Oncology Poster 8E (2011), 1 page.
Patnaik et al., "EZN-2208, a novel anticancer agent, in patients with advanced malignancies: a Phase 1 dose escalation study," American Association for Cancer Research Poster C221 (2009), 1 page.
Poujol et al., "Sensitive HPLC-Fluorescence Method for Irinotecan and Four Major Metabolites in Human Plasma and Saliva: Application to Pharmacokinetic Studies," Clinical Chemistry (2003) 49:1900-1908.
Seo et al., "The pharmacokinetics of Zr-89 labeled liposomes over extended periods in a murine tumor model," Nucl Med Biol. (2015) 42(2):155-163, 24 pages.

* cited by examiner

Figure 2

(Prior Art)

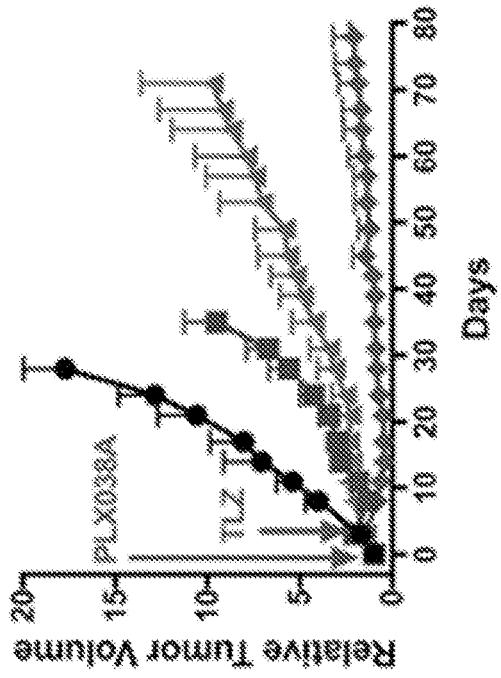
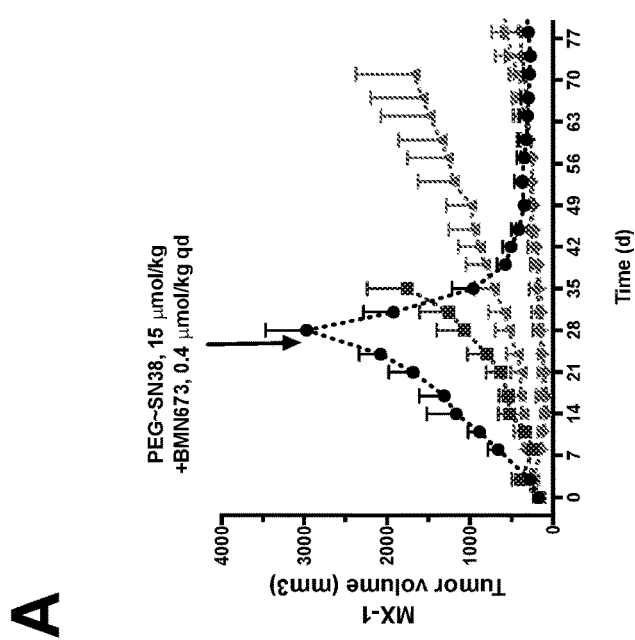
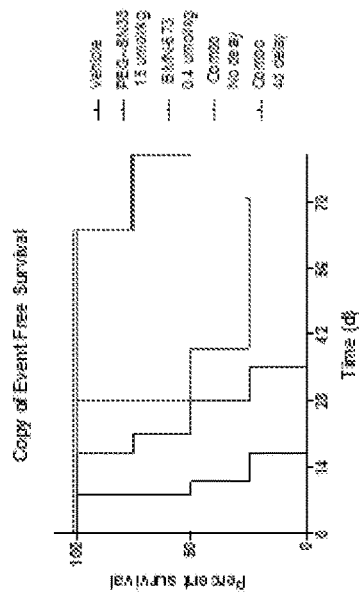

A) Tumor volume vs time; vehicle control (●), and after single i.p. injection of 15 μmol/kg PLX038A (■), daily oral gavage of 0.4 μmol/kg BMN673 (▲), or combination therapy of a single i.p. dose of 15 μmol/kg PLX038A with daily oral BMN673 starting on the same day (▼) or 4 days later (♦). When the vehicle control tumors reached ~3,000 mm$^3$, animals were treated with the combination, but BMN673 dosing was started immediately (○). Data are plotted as mean tumor volumes ± SEM. Groups had N=4 animals. B) As in A, except daily TLZ initiated 4 days after PLX038A dosing (♦). C) Event-free survival where an event is defined as a 4-fold increase over tumor size on day 0.

Figure 3

SYNERGISTIC CANCER TREATMENT

CROSS-REFERENCE TO RELATED APPLICATIONS

This application is a national stage application under 35 U.S.C. § 371 of International Application No. PCT/US2019/013314, filed internationally on Jan. 11, 2019, which claims priority from U.S. provisional application 62/617,095 filed 12 Jan. 2018, U.S. provisional application 62/674,483 filed 21 May 2018, U.S. provisional application 62/711,421 filed 27 Jul. 2018, U.S. provisional application 62/716,788 filed 9 Aug. 2018, U.S. provisional application 62/716,796 filed 9 Aug. 2018, U.S. provisional application 62/700,147 filed 18 Jul. 2018, and U.S. provisional application 62/711,423 filed 27 Jul. 2018, the disclosures of which are herein incorporated by reference in their entirety.

TECHNICAL FIELD

The invention relates to use of topoisomerase I inhibitors linked to a macromolecule through a linkage that undergoes beta elimination for the treatment of cancer. More specifically, it concerns topoisomerase I inhibitor treatment of subjects having cancer where the pharmacokinetics are suitably controlled, said subjects having either a genetic defect in a DNA damage response (DDR) and/or said treatment involves administering a topoisomerase I inhibitor in combination with an inhibitor of DDR or in combination with a cell cycle checkpoint inhibitor. In some embodiments, the invention entails the exploitation of synthetic lethal interactions in cancer cells, where a defect in a gene necessary for DDR causes a second gene to become essential for cell survival.

BACKGROUND ART

Topoisomerase I inhibitors are well known for treatment of various cancers, as they are inhibitors of the essential ligation step catalyzed by topoisomerase I to remedy single strand DNA damage that occurs due to relief of tension caused by supercoiling in DNA replication. (DNA replication requires topoisomerase I.) Topoisomerase I inhibitors include camptothecin and analogs thereof. Many of these compounds are approved and used in chemotherapy in the treatment of a wide variety of cancers.

In cancer cells with certain genetic defects the administration of a topoisomerase I inhibitor has been observed to have enhanced efficacy as compared to cancer cells without such defects. For example, one topoisomerase inhibitor, SN-38, has been administered as a conjugate with polyethylene glycol in BRCA1-deficient mice with mammary tumors and not only is the combination of BRCA1 deficiency with the inhibition by SN-38 of topoisomerase effective, but it also overcomes ABCG2 mediated resistance. See, for example, Zander, S. A. L. et al., PLOS One (2012) 7:e45248. In addition, various topoisomerase inhibitors have been administered in combination with additional anticancer agents that are DDR inhibitors and/or cell cycle checkpoint inhibitors. See, for example, Abal, M. et al., Oncol. Gene (2004) 23:1737-1744, Wainberg, Z. A. et al., Targ Oncol. (2017) 12:775-785; Verschraegen, C. F. et al., Cancer (2013) 5:418-429; and Gray, J. et al., Cancer Biol. and Ther. (2012) 13:614-622; Josse, R et. al, Cancer Res (2014) 74:6968-6978; Ma, C. X., et al, Breast Cancer Res Treat (2013) 137:483-492. In vitro studies have also shown that inhibiting expression of a protein important in DNA replication and repair, Werner Syndrome helicase (WRN) enhances the effect of irinotecan on cancer cells. See Futami, K., et al., Biol Pharm Bull (2007) 30:1958-1961. Combination of cell checkpoint inhibitors with various DNA damaging drugs has also been tested in clinical trials. (See, Visconti, R. et al., J. Exp. Clin. Cancer Res. (2016) 35:153.)

In addition, there is extensive knowledge of the landscape of DNA damage response deficiencies across various genes and genome locations (see Knijnenburg, T. A. et al., Cell Reports (2018) 23:239-254.

Coupling of topoisomerase I inhibitors, including SN-38, to macromolecules has been reported by Zhao, H. et al., Bioconjugate Chem. (2008) 19:849-859 and Koizumi, F. et al., Cancer Res. (2006) 66:10048-10056. A particular set of conjugates useful in the invention is disclosed by Santi, D. V. et al., J. Med. Chem. (2014) 57:2303-2314. An additional conjugate commonly denoted NKTR-102, which is a PEGylated irinotecan, is also known.

The present invention provides improved methods of treatment with topoisomerase I inhibitors in tumor subjects, which methods take advantage of either an inherent defect in DDR of a subject either associated with a germline mutation or other dysfunction in the cancer cells of the subject or combination treatment with additional agents that result in synthetic lethality.

DISCLOSURE OF THE INVENTION

As evidenced by the literature cited above, it is known that topoisomerase I is essential for DNA replication, which is essential for cell growth and for replication. Inhibitors of topoisomerase I, such as irinotecan and its active metabolite, SN-38, have been used to treat cancer by inhibiting successful DNA replication.

There are also reports of attempts to combine topoisomerase I inhibitors with either a cell cycle checkpoint inhibitor (which neutralizes the mechanism by which cells determine that replication has or has not been successfully accomplished) or an additional inhibitor of DNA damage response (DDR). It is also known to administer topoisomerase I inhibitors to cancers already characterized as deficient in DDR.

Some such attempts have involved topoisomerase I inhibitors coupled to a solubilizing agent such as polyethylene glycol (PEG). However, the pharmacokinetics of the inhibitors thus far provided have not been appropriate to obtain a successful result and toxicity of these inhibitors has also been problematic.

The protocols of the invention are most importantly performed in human subjects, although the invention is also applicable to other mammalian subjects, including laboratory models for testing disease treatments. The protocols are also useful in livestock and companion animals.

It has now been found that by providing a topoisomerase I inhibitor with a linkage to a macromolecule that decouples through beta elimination, the pharmacokinetics can be adjusted to provide more effective and tolerable treatments in a subject having a defect in DDR, or in combination with inhibitors of a cell cycle checkpoint pathway and/or with an inhibitor of DDR. The conjugates of the invention can also be administered in doses that mitigate the synergistic toxicity of topoisomerase I inhibitors with such additional agents.

Thus, in a first aspect, the invention is directed to a method to treat cancer in a subject in need of such treatment, said subject having been identified as having one or more defects in DNA damage response (DDR). The method comprises administering to the subject an effective amount of a topoisomerase I inhibitor coupled to a macromolecule through a linker that provides decoupling through a beta elimination mechanism.

In a second aspect, the invention is directed to a method to treat cancer in a subject, which comprises administering to the subject an effective amount of a topoisomerase I inhibitor coupled to a macromolecule through a linker that provides decoupling through a beta elimination mechanism in combination with an effective amount of an additional inhibitor of DDR.

In a third aspect, the invention is directed to a method to treat cancer in a subject, which comprises administering an effective amount of a topoisomerase I inhibitor coupled to a macromolecule through a linker that provides decoupling through a beta elimination mechanism in combination with an effective amount of a cell cycle checkpoint pathway inhibitor.

In the first aspect of the invention, the method may also include a procedure to diagnose the subject for the presence of the defect; and in embodiments where more than one agent (including the invention conjugates) is administered, the coadministration of more than one agent may be simultaneous or in sequence in either order of the agents. The difference in time of administration of coadministered agents may be as long as days. The agents may also optionally be administered in the same composition.

Combinations of the forgoing approaches are also included within the invention; thus, a subject inherently having a defect in DDR may be supplied the conjugated topoisomerase I inhibitor coupled to a macromolecule through a linker that provides decoupling through a beta elimination mechanism in combination with either an additional DDR inhibitor or a checkpoint pathway inhibitor or both. Independently, regardless of whether the subject exhibits an inherent defect in DDR, a combination of the topoisomerase I inhibitor conjugate of the invention with either or both an additional DDR inhibitor and a cell cycle checkpoint inhibitor is included within the scope of the invention. In addition, use of more than one DDR inhibitor and/or more than one cell cycle checkpoint inhibitor in combination with the topoisomerase I inhibitor conjugate is included in the scope of the invention.

BRIEF DESCRIPTION OF THE DRAWINGS

Figure 2:
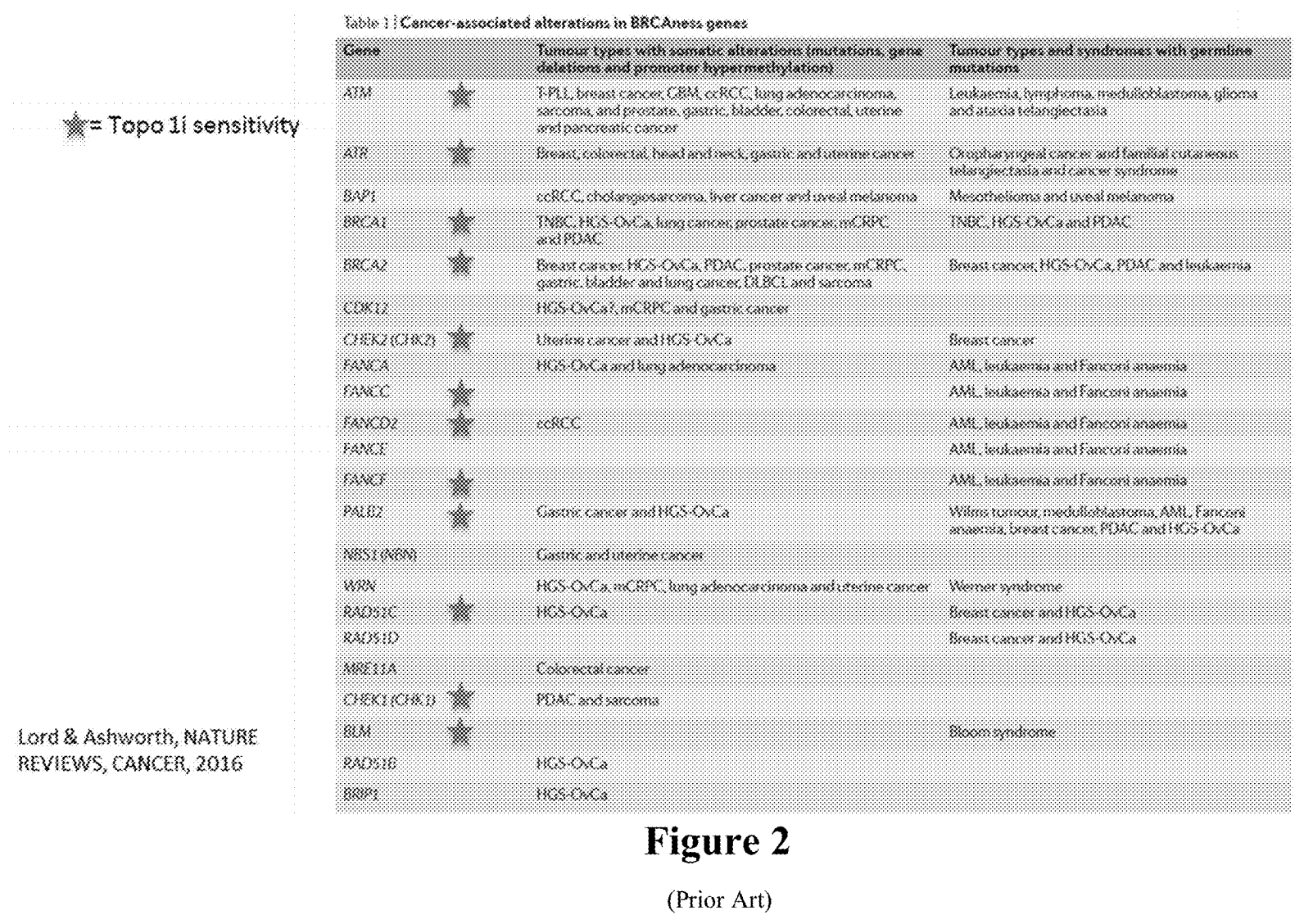

FIG. 2 shows the state of the art with regard to sensitivity to topoisomerase I inhibitors of various DDR defects, both with respect to germline in non-germline DDR associated with various genes.

FIGS. 3A-3C show the synergistic effect of an SN-38 conjugate of the invention with an inhibitor of PARP on tumor growth and on event free survival.

MODES OF CARRYING OUT THE INVENTION

Figure 1:
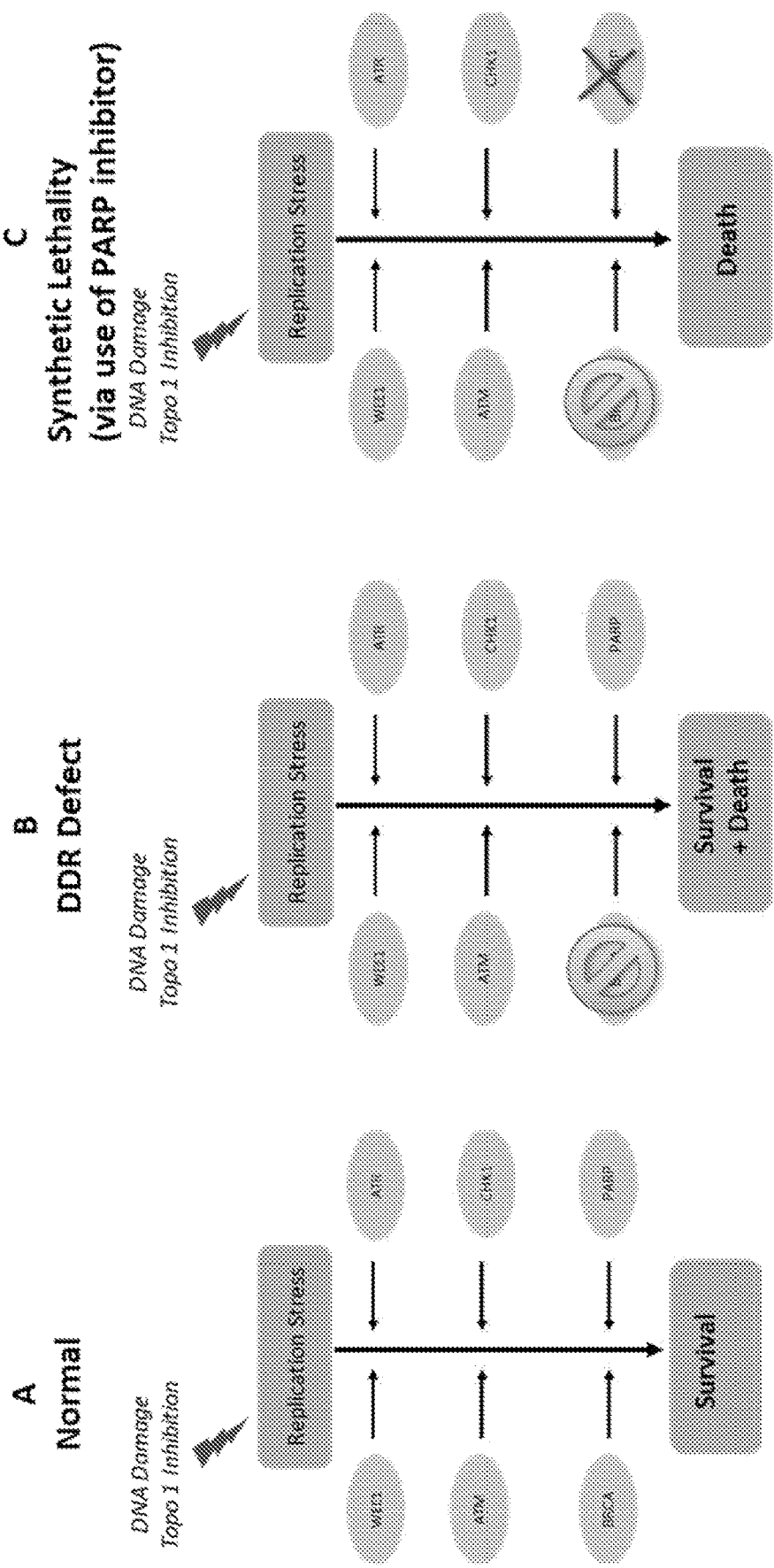
FIG. 1 shows a schematic outline of the invention approach wherein single treatment with topoisomerase I inhibitor may be offset by various repair or cell cycle checkpoints as in panel A. When the subject has an inherent DDR defect, e.g., a mutation in the BRCA gene as in panel B, the effect of topoisomerase I inhibition is strengthened, and this is further strengthened by an inhibitor of DNA damage repair such as a PARP inhibitor as in panel C (PARP is poly ADP ribose polymerase).

The invention takes advantage of synergistic attacks on the DNA damage response that might be mounted in cancer cells to affect their successful replication. The topoisomerase I inhibitor conjugates that cause DNA damage may be combined with either inhibitors of DDR or other inhibitors that interfere with DNA damage repair or replication. The DDR is an extremely complex process involving various mechanisms of fixing DNA to correct errors that occur either through mutation or through errors in the replication process itself. Part of this response is also a control mechanism involving cell cycle checkpoints that ensures that DNA is properly repaired or replicated before the cell divides or alternatively to effect apoptosis so that error-ridden DNA is not transmitted to daughter cells. The present invention employs a combination of a particular DDR inhibitor—a topoisomerase I inhibitor with other obstacles to successful replication including other inhibitors of DDR and inhibitors of cell cycle checkpoint pathways including instances wherein the cancer cells themselves are defective in their ability to respond to DNA damage.

The invention utilizes a conjugate of a topoisomerase I inhibitor coupled to a macromolecule through a linker that provides decoupling through a beta elimination mechanism. Suitable topoisomerase I inhibitors are typically camptothecin and analogs, including irinotecan, otherwise known as CPT-11, and its active metabolite, SN-38, as well as topotecan, 9-amino-camptothecin, and water soluble analogs, such as GI 147211 and GI 149893.

In some embodiments, the macromolecule is a linear or branched or multi-armed, polyethylene glycol.

Particularly preferred is a conjugate of formula (I)

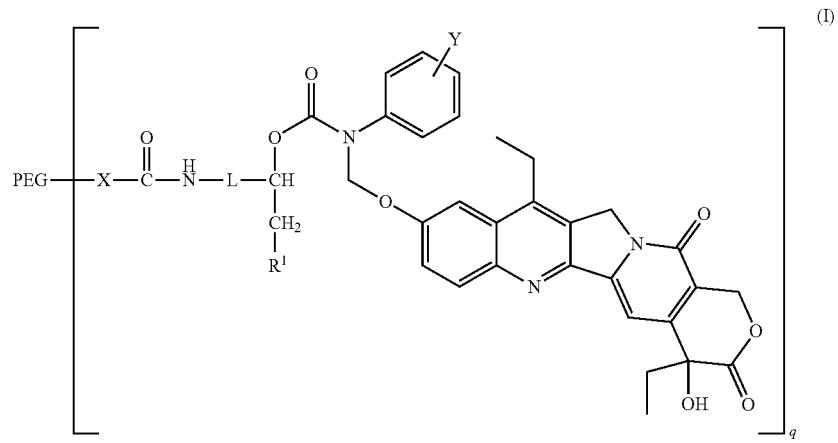

wherein

PEG is linear or branched and, when q is 2-8, multi-armed, polyethylene glycol;

X is $(CH_2)_m$, wherein m=1-6;

L is $(CH_2CH_2O)_p(CH_2)_r$, wherein r=1-10 and p=0-10;

$R^1$ is CN or $SO_2NR^2{}_2$, wherein each $R^2$ is independently alkyl, aryl, heteroaryl, alkylalkenyl, alkylaryl, or alkylheteroaryl, or two $R^2$ taken together can form a ring;

Y is $COR^3$ or $SO_2R^3$, wherein $R^3$=OH, alkoxy, or $NR^4{}_2$, wherein each $R^4$ is independently alkyl, substituted alkyl, or two $R^4$ taken together can form a ring; and q is 1-8.

In particular, this conjugate may have a PEG of average molecular weight 30,000-50,000 Da, and/or wherein q=4, and/or wherein $R^1$=CN or $SO_2NR^2{}_2$ wherein each $R^2$ is alkyl.

The conjugate may be of the formula:

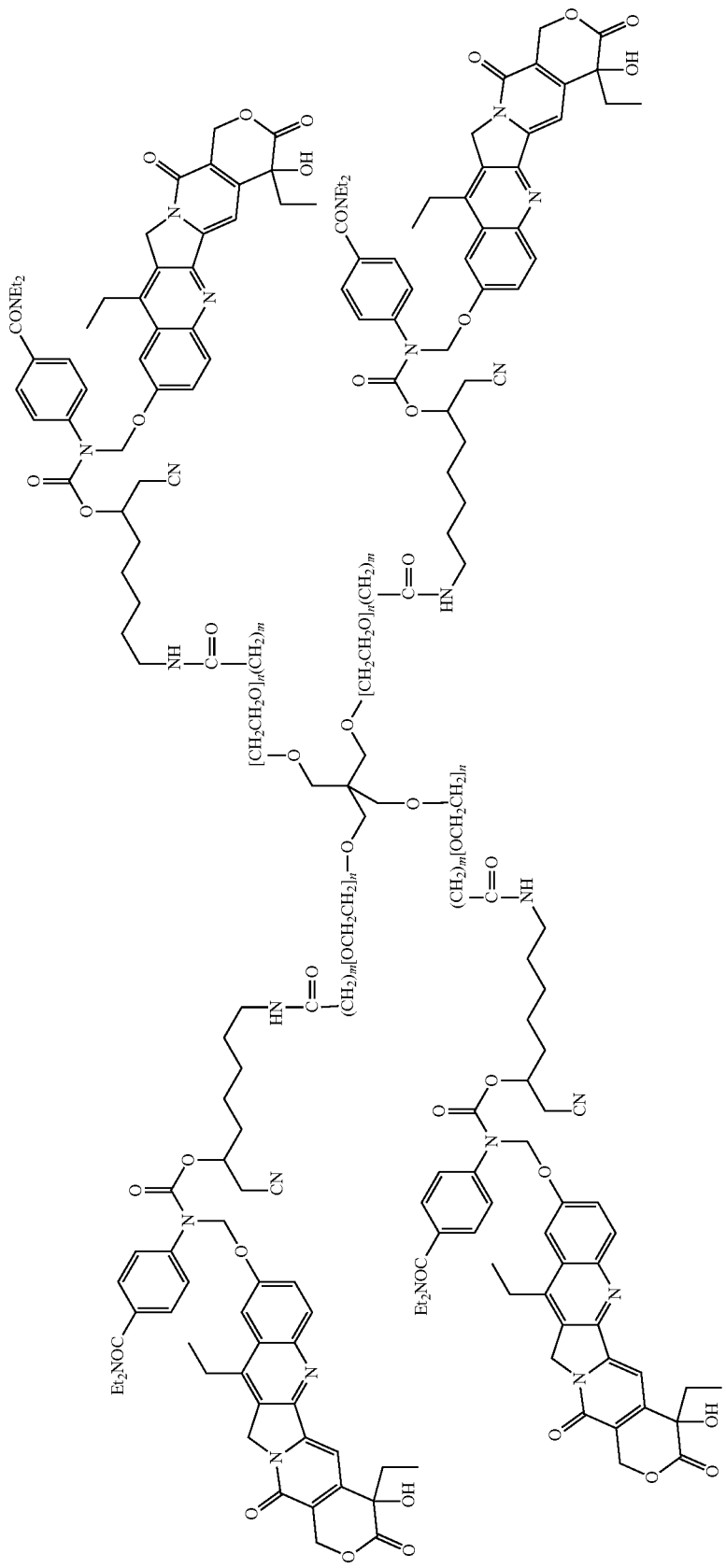

wherein m=1-6 and n is 200-250.

In particular, the conjugate may be PLX038, which is of the above formula where m is 1 and n is approximately 225.

The conjugates useful in the invention are generally provided in standard pharmaceutical formulations in combination with one or more pharmaceutically acceptable excipients, in some cases wherein the pH is between 4.0 and 6.0. Standard formulations can be found, for example, in Remington Pharmaceutical Sciences, Latest Edition, Mack Publishing Company, Easton, Pa.

The invention is based on the favorable properties of a conjugate that has suitable pharmacokinetics for combination with either endogenous DDR defects or with coadministered compounds that are cell cycle checkpoint inhibitors or DDR inhibitors.

In some embodiments, the conjugates, when administered to subjects provide a continuous low dose exposure to the topoisomerase I inhibitor wherein the concentration of the free inhibitor can be maintained between 15 and 5 nM between once or twice weekly administrations or over a protocol of administration, for example, of once every two weeks. In any case, the conjugates provide consistent low dose exposure to the active drug.

As to the identity of the coadministered DDR inhibitors and/or cell cycle checkpoint inhibitors, many are known in the art as set forth, for example, in the Background Art discussion above.

Cell cycle checkpoints include G1-S, S, and G2/M. Any of these can be targeted in combination with the topoisomerase I inhibitor conjugate, and/or in combination with additional agents that target components needed for successful checkpoint transition. This may be also against a background of an endogenous defect in cell cycle checkpoint control.

Suitable cell cycle checkpoint targets include checkpoint kinase 1 or 2 (CHK1 or CHK2), ataxia telangiectasia mutated (ATM) kinase, ataxia telangiectasia and Rad3 related (ATR) kinase, Wee1 kinase and p53. An extensive list of inhibitors of these targets is found in WO2012/074754.

Suitable DDR inhibitors include those that target homologous recombination (HR), e.g. poly(ADP-ribose) polymerase (PARP) inhibitors and/or other DDR pathways, including an HEJ, HR, alt-NHEJ/MMEJ, SSA, ICL, SSB, BER, TLS, NER and MMR. A large number of agents are in development for addressing these targets, and a number of agents known to do so are now used in the clinic.

All documents cited are incorporated herein by reference in their entirety.

The following example is intended to illustrate, but not limit the invention.

Example 1

Synergistic Effect of PLX038A and PARP Inhibitor Talazoparib (Designated BMN673 or TLZ)

Preparation of murine MX-1 xenografts: The MX-1 cell line was obtained from Charles River Labs (Frederick, Md.).[1] Cells were cultured in RPMI-1640, 10% FBS and 1% 2 mM L-glutamine at 37° C. in 95% air/5% $CO_2$ atmosphere.

[1] Ovejera A A et al. Chemotherapy of human tumor xenografts in genetically athymic mice. Ann Clin Lab Sci 8: 50-6, 1978.

Female NCr nude mice (N CrTac:NCr-Foxnt1$^{nu}$; ~6-7 weeks old) from Taconic Bioscience (Cambridge City, Ind.) were housed at the UCSF Preclinical Therapeutics Core vivarium (San Francisco, Calif.). All animal studies were carried out in accordance with UCSF Institutional Animal Care and Use Committee. Tumor xenografts were established by subcutaneous injection with MX-1 tumor cells ($2\times10^6$ cells in 100 μl of serum free medium mixed 1:1 with Matrigel) into the right flank of female NCr nude mice. When tumor xenografts reached 1000-1500 mm$^3$ in donor mice, they were resected, cut into even-size fragments (~2.5×2.5×2.5 mm in size), embedded in Matrigel and re-implanted via subcutaneous trocar implantation in receiver mice.[2]

[2] Morton C L, Houghton P J. Establishment of human tumor xenografts in immunodeficient mice. Nat Protoc. 2007; 2(2):247-50.

Dosing and tumor volume measurements: Solutions of PLX038A (1.02 mM SN38; 0.26 mM PLX038A conjugate) were prepared in pH 5 isotonic acetate and sterile filtered (0.2 μm) before use. Solutions of BMN673 (52 μM) were prepared in 10% dimethylacetamide/5% Solutol HS15/85% 1×PBS and were sterile filtered (0.2 μm) before use.

Groups (N=4-5/group) were dosed when the group average reached 100-200 mm$^3$ in size. Mice received vehicle, a single dose of PLX038A (14.7 mL/kg i.p., 15 μmol/kg), daily doses of BMN673 (7.72 mL/kg p.o., 0.4 μmol/kg), or a combination of PLX038A and BMN673 at the same doses. For groups receiving the combination, daily BMN673 dosing began on the same day (FIG. 3A) or after a 4-day delay (FIG. 3B) after dosing PLX038A. Tumor volumes (caliper measurement: 0.5×(length×width$^2$)) and body weights were measured twice weekly. When vehicle control tumors reached ~3000 mm$^3$ in size, mice were treated with the combination of a single dose of PLX038A (15 μmol/kg) and daily BMN673 (0.4 μmol/kg) combination with no delay between dosing (FIG. 3A).

As shown in FIGS. 3A and 3B, administration of PLX038A to mice bearing MX-1 tumors at 15 μmol/kg in combination with daily doses of Talazoparib at 0.4 μmol/kg provides a synergistic effect as compared to either of these drugs alone. This was true whether daily dosage with TLZ began at the same time as PLX038A or 4 days later. A single combination administered to control immediately reduced tumor volume (FIG. 3A).

As shown in FIG. 3C, event-free survival was enhanced synergistically with the combination vs PLX038A and TLZ individually.

Example 2

Synergy of PLX038A and Tumor Cell Defect

Figure 4:
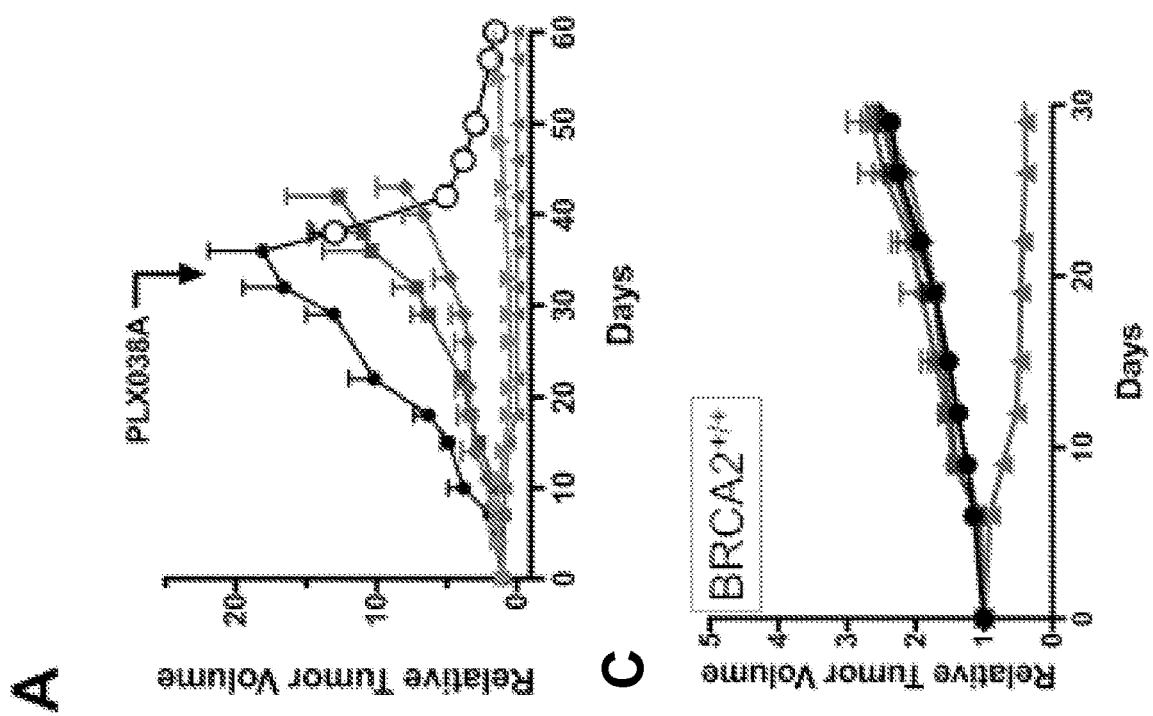
FIGS. 4A-4C show the impact of BRCA 1 or BRCA 2 deficiency on effectiveness of the SN-38 conjugate in treating tumors in mice.

MX-1 cells are BRCA 1 deficient and CAPAN-1 cells are supplied as either BRCA 2 deficient (−/−) or not deficient (+/+). The general protocol of Example 1 was followed with mice bearing tumors of these cell lines. For mice with MX-1 tumors, dosages were single i.p. injections of 137 μg/kg of irinotecan or 4, 40 or 120 μg/kg of PLX038A. For mice with CAPAN-1 xenografts, dosages were single i.p. injections of 137 μg/kg irinotecan or 15, 40 or 120 μg/kg of PLX038A. FIGS. 4A-4C show the results of these dosages on tumor volumes, which were measured twice weekly.

As shown in FIG. 4A, all dosages of PLX038A were more effective than irinotecan in reducing tumor volume, with 40 or 120 μg/kg essentially stopping tumor growth. Also shown is the dramatic result of a single dose of 120 μg/kg PLX038A administered when the control tumors reached 2000 mm$^3$.

A comparison of FIGS. 4B and 4C shows the effect of BRCA 2 deficiency on the effectiveness of treatment with irinotecan or PLX038A—only the very highest dose of PLX038A was comparably effective for both deficient and non-deficient cells. The effectiveness of all other dosage levels was enhanced in the BRCA 2 deficient cells.

The invention claimed is:

1. A method to treat cancer in a subject in need of such treatment, which method comprises administering to said subject an effective amount of a conjugate of the topoisomerase I inhibitor SN-38 coupled to a macromolecule through a linker, in combination with an effective amount of a poly(ADP-ribose) polymerase (PARP) inhibitor, wherein said conjugate has the following formula:

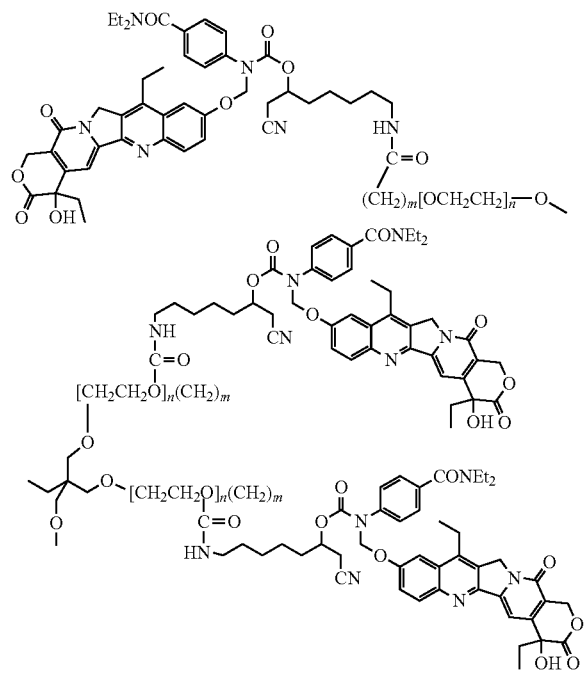

-continued

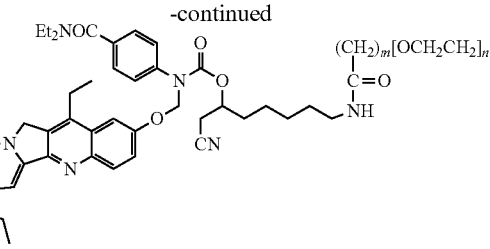

wherein m=1-6 and n=200-250.

2. The method of claim 1 wherein m is 1 and n is about 225.

3. The method of claim 1, wherein the subject has a genetic defect in a DNA damage response (DDR).

4. The method of claim 2, wherein the subject has a genetic defect in a DNA damage response (DDR).

5. The method of claim 1, wherein the subject is a human.

6. The method of claim 2, wherein the subject is a human.

7. The method of claim 1, wherein the conjugate and the PARP inhibitor are administered simultaneously.

8. The method of claim 2, wherein the conjugate and the PARP inhibitor are administered simultaneously.

9. The method of claim 1, wherein the conjugate and the PARP inhibitor are administered sequentially.

10. The method of claim 2, wherein the conjugate and the PARP inhibitor are administered sequentially.

* * * * *